US00PP15717P2

(12) United States Plant Patent
Kordes

(10) Patent No.: US PP15,717 P2
(45) Date of Patent: Apr. 12, 2005

(54) MINIATURE ROSE PLANT NAMED 'KORGLOLEV'

(50) Latin Name: *Rosa hybrida*
Varietal Denomination: KORglolev

(75) Inventor: Tim-Hermann Kordes, Munich (DE)

(73) Assignee: W. Kordes' Sŏhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 10/737,664

(22) Filed: Dec. 15, 2003

(30) Foreign Application Priority Data

Apr. 23, 2001 (QZ) ..... PBR 20019999

(51) Int. Cl.[7] ..... A01H 5/00
(52) U.S. Cl. ..... Plt./121
(58) Field of Search ..... Plt./121, 116, 128

(56) References Cited

U.S. PATENT DOCUMENTS

PP11,363 P * 4/2000 Kordes ..... Plt./122

FOREIGN PATENT DOCUMENTS

QZ 20022094 12/2002
QZ 12903 4/2004

* cited by examiner

*Primary Examiner*—Anne Marie Grunberg
*Assistant Examiner*—June Hwu

(57) ABSTRACT

A new and distinct variety of miniature rose with long lasting, novel pink flowers, and dark green and attractive foliage. It exhibits compact, uniform growth and flowering under greenhouse conditions when grown as a potted floral plant. The new variety propagates well from cuttings and by grafting. This new and distinct variety has shown to be uniform and stable in the resulting generations from asexual propagation.

1 Drawing Sheet

Genus, species and variety denomination: The botanical classification of the new rose plant is *Rosa hybrida,* variety denomination, 'KORglolev'.

BACKGROUND OF THE INVENTION

The new variety of miniature rose plant of the present invention originated from a controlled crossing in a breeding program between 'KORengir', a non-patented rose, and 'KORfrauma' a patented rose variety by the same breeder described and illustrated in U.S. Plant Pat. No. 11,363 issued on Apr. 25, 2000.

The two parents were crossed and the resulting seeds were planted in a controlled greenhouse environment. The resulting seedlings exhibited distinctive physical and biological characteristics. The new rose plant was selected in June, 2000 as a single plant from the seedling beds due to its superior characteristics and asexually propagated for further evaluation. This new and distinctive miniature rose variety is named 'KORglolev'.

SUMMARY OF THE INVENTION

The new rose plant may be distinguished from its seed parent, KORengir, by the following combination of characteristics:

1. The flowers of the seed parent are Red Group 39A, while the flowers of KORglolev are Red Group 52B.
2. KORglolev lacks complete reproductive parts, while KORengir has complete flowers.

The new rose plant may be distinguished from its pollen parent, KORfrauma by the following combination of characteristics:

1. The flowers of the pollen parent have petals with Red Group 43A for the upper surface and Red Group 53B for the lower surface; while the flowers of KORglolev are Red Group 52B.
2. KORglolev lacks complete reproductive parts, while KORfrauma has complete flowers.

The objective of the hybridization was to create a new and distinct rose plant with unique qualities, such as:

1. Compact and uniform growth and flowering under greenhouse conditions when grown as a potted floral plant;
2. Abundant, long lasting, and attractive flowers on upright stems;
3. Resistance to diseases encountered in greenhouse and nursery culture; and
4. Suitability for production from softwood cuttings in floral and nursery containers;

This combination of traits is not present in prior rose cultivars. These objectives have been substantially achieved and distinguish 'KORglolev' from all other varieties of which we are aware. The new cultivar may be distinguished from other pot rose cultivars by its disease resistance, abundant, bright pink flowers, and extremely compact growth making the KORglolev suitable for commercial greenhouse production in 6 to 8 cm pots without growth regulation.

As part of the rose development program, Tim-Hermann Kordes germinated the seeds from the aforementioned hybridization and conducted evaluations and observations on the resulting seedlings in a controlled environment in Sparrieshoop, Germany. Asexual reproduction of 'KORcarill' by softwood cuttings was first done Jul. 1, 2000 at the Rosa-Danica Nursery in Odense, Denmark.

This initial and other subsequent propagations conducted in controlled environments show that the foregoing and all other characteristics of 'KORglolev' come true to form and are transmitted through succeeding generations.

BRIEF DESCRIPTION OF THE DRAWING

The accompanying color illustration, SHEET ONE, shows as true as is reasonably possible to obtain in color photographs of this type, the typical characteristics of the buds, flowers, foliage and habit 'KORglolev'.

DETAILED DESCRIPTION

The following is a description of 'KORglolev', as observed in its growth in greenhouses in Grimsby, Canada on plants of 12 weeks of age and in a field nursery in Sparrieshoop, Germany on plants of 1 year of age. Color references are made using The Royal Horticultural Society (London, England) Colour Chart, 2001 except where common terms of color are used.

For a comparison, several physical characteristics of the rose variety 'KORfrauma', a rose variety from the same inventor described and illustrated in U.S. Plant Pat. No. 11,363 and issued on Apr. 25, 2000 are compared to 'KORglolev' in Chart 1.

CHART 1

| | 'KORglolev' | 'KORfrauma' |
|---|---|---|
| Flower diameter, open. | 40 mm. | 38–40 mm. |
| Reproductive parts | Incomplete and generally lacking. | Complete. |

Parents:
- *Seed parent.*—KORengir.
- *Pollen parent.*—KORfrauma.

Classification:
- *Botanical classification.*—*Rosa hybrida.*
- *Commercial classification.*—Miniature.

FLOWER AND FLOWER BUD

Blooming habit: Recurrent.

Flower bud:
- *Size.*—Upon opening, 20 mm in length from base of receptacle to end of bud.
- *Bud form.*—Semi-ovoid.
- *Bud color.*—As sepals first unfold, bud color is Red Group 52B. When ½ open, the upper surface of petals is Red Group 52B, and the lower surface is Red Group 52B.

Sepals:
- *Size.*—25–35 mm long×4–6 mm wide. The longest sepals have the most pronounced foliaceous appendages.
- *Margins.*—Moderate foliaceous appendages on three of the five sepals.
- *Quantity.*—Five.
- *Surface texture.*—Light to moderately pubescent. Stipitate glands are present on only a few of the sepals.
- *Color.*—Dark green. Upper surface Green Group Green Group 138A–139A. Lower surface Green Group 138B–C.

Receptacle:
- *Surface.*—Nearly smooth. With limited numbers of white hairs.
- *Color.*—Green Group 138A.
- *Shape.*—Vase shaped.
- *Size.*—7 mm (h)×5 mm (w).

Peduncle:
- *Surface.*—Nearly smooth. With limited numbers of white hairs.
- *Length.*—30–50 mm average length.
- *Diameter.*—1.0–1.2 mm.
- *Color.*—Green Group 138A.
- *Strength.*—Upright, with average strength.

Borne: Singly and/or in small clusters. 1–3 buds per flowering stem.

Flower bloom:
- *Fragrance.*—Little to none.
- *Duration.*—The blooms have a duration on the plant of approximately 21 to 24 days. As a cut flower 10 to 14 days.
- *Size.*—Medium for a 8–11 cm pot rose. Average flower diameter is 40 mm when open.
- *Form.*—Shape of flower when viewed from the side: Upon opening, upper part: Flattened convex. Upon opening, lower part: Convex. Open flower, upper part: Flat to Flattened convex. Open flower, lower part: Flattened convex.

Color:
- *Upon opening, petals.*—Outermost petals: Outer Side: Red Group 52B–C. Inner Side: Red Group 52B–C. Innermost petals: Outer Side: Red Group 52B. Inner Side: Red Group 52B.
- *Upon opening, basal petal spots.*—Basal petal spot: Outer Side: Green-Yellow Group 1D. Inner Side: Green-Yellow Group 1D.
- *After opening, petals.*—Outermost petals: Outer Side: Red Group 52C–D. Inner Side: Red Group 52C. Innermost petals: Outer Side: Red Group 52B–C. Inner Side: Red Group 52B–C.
- *After opening, basal petal spots.*—Basal petal spot: Outer Side: Green-Yellow Group 1D. Inner Side: Green-Yellow Group 1D. Variegations: None.

General tonality: On open flower Red Group 52B. No change in the general tonality at the end of the $6^{th}$ day. Afterwards, Red Group 52C–D.

Petals:
- *Petal count.*—Approximately 50 to 60 petals under normal conditions.
- *Petal reflex.*—Inner petals reflex somewhat. Outermost petals double reflexed on open blooms.
- *Petal edge.*—Entire.
- *Petal shape.*—Rounded. Shape of Base: Obovate. Shape of Apex: Nearly round.
- *Surface texture.*—Smooth.
- *Petal size.*—14–18 mm long; 10–18 mm wide.
- *Thickness.*—Average.
- *Petal arrangement.*—Generally in a regular pattern with overlapping edges.
- *Petaloids.*—Present. Quantity: 8–12. Size: 4.0–8.0 mm long; 3.0–5.0 mm. wide. Texture: Smooth. Shape: Linear to narrowly oblanceolate, with variable apex and narrow base. Color: Inner and outer side Red Group 52B.

Reproductive organs:
- *Pistils.*—Generally absent. Limited numbers of flowers exhibit a few incomplete pistils. When present, upright and Yellow-Green Group 154D in color.
- *Stamens.*—Absent.

THE PLANT

Plant growth: Vigorous. Compact to bushy. When grown as a 8–11 cm pot plant, the average height of the plant itself is 18 cm and the average width is 16–18 cm. When grown as a budded nursery plant the average plant height is 30 cm and the average plant width is 30 cm.

*Stems.*—

*Stem color.*—Young wood: Yellow Group 146A. Older wood: Yellow Group 146A.

*Stem surface.*—Young wood: Smooth. Older wood: Smooth.

Prickles: Present.

*Incidence.*—Approximately 4 prickles per 10 cm of stem, spaced evenly along the stem.

*Size.*—Average length: 3 mm–5 mm.

*Color.*—Yellow-Green Group 146A to Green Group 138A at the base and middle. The distal end exhibits intonations of Greyed-Red Group 180D.

*Shape.*—Linear.

Leaves and leaflets: Normally 5 leaflets on normal leaves in middle of the stem.

*Leaf size.*—65–80 mm (l)×38–42 mm (w).

*Quantity.*—Abundant.

*Glossiness on upper side.*—Glossy.

*Color, mature foliage.*—Upper Leaf Surface: Green Group 138A–139A. Lower Leaf Surface: Yellow-Green Group 146A.

*Color, juvenile foliage.*—Upper Leaf Surface: Green Group 138A–139A. Lower Leaf Surface: Yellow-Green Group 146A with intonations of Greyed-Red Group 183B–C.

*Stipules.*—Size: 7 to 8 mm average length. Stipule color: Yellow-Green Group 146A. Presence of stipitate glands: Moderate numbers present on margins.

*Petiole.*—Length: 8 mm–12 mm. Diameter: 1.1–1.4 mm. Petiole color: Yellow-Green Group 147A–B. Some intonations of Greyed-Red Group 183B–C, generally on the prickles. Prickles: A limited number of small prickles. Stipitate glands: Present on margins. Other: Limited numbers of fine white hairs underneath.

*Rachis.*—Rachis color: Yellow-Green Group 147A–B. Some intonations of Greyed-Red Group 183B–C; generally on the prickles. Prickles: A limited number of small prickles. Stipitate glands: Present on margins. Other: Limited numbers of fine white hairs underneath.

*Leaflets.*—Leaflet shape: Pointed oval. Average Size of Terminal Leaflet: 20–22 mm long; 12–16 mm wide. Margins: Serrated. Texture: Average thickness.

Hips/seed formation: None observed. The plant has not been grown to the stage of hip and seed development due to its use as a flowering potted plant.

Winter hardiness: Due to the variety's principal use in greenhouses, winter hardiness has not been evaluated.

Disease resistance: Above average resistance to mildew and *Botrytis* under normal growing conditions in Odense, Denmark.

I claim:

1. A new and distinct variety of miniature rose plant characterized by the following combination of characteristics:

(a) forms abundant, attractive pink long lasting flowers;

(b) exhibits a compact and bushy growth habit;

(c) is suited for growing in greenhouse in pots from softwood cutting, and;

(d) exhibits durable flowers and foliage suitable for distribution in the floral industry;

substantially as herein illustrated and described.

* * * * *

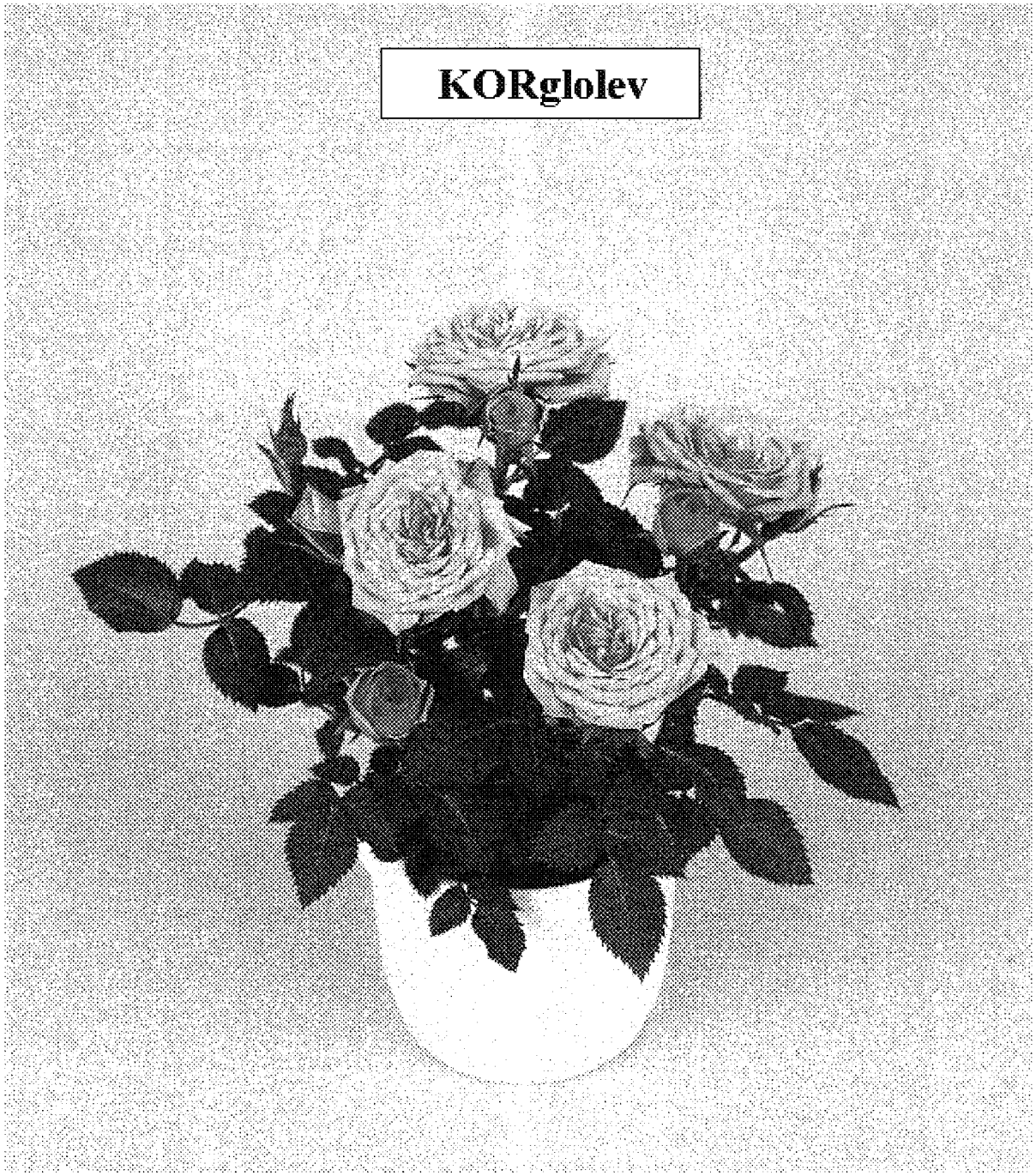
KORglolev